United States Patent [19]

Elmore

[11] Patent Number: 4,645,682

[45] Date of Patent: * Feb. 24, 1987

[54] METHOD AND COMPOSITION FOR TREATMENT OF PLANTS

[76] Inventor: Charles D. Elmore, 570 Ridgewood Ave., Gainesville, Ga. 30503

[*] Notice: The portion of the term of this patent subsequent to Jan. 24, 2003 has been disclaimed.

[21] Appl. No.: 537,658

[22] Filed: Sep. 30, 1983

[51] Int. Cl.$^4$ .......................... A01G 5/06; A01N 1/00; A01N 3/00; A01B 79/00

[52] U.S. Cl. .......................................... 427/4; 8/518; 47/58; 71/3

[58] Field of Search ............... 47/1 R, 58; 8/518, 519; 427/4; 71/3

[56] References Cited

U.S. PATENT DOCUMENTS

| | | | |
|---|---|---|---|
| 3,157,964 | 11/1964 | Ferguson et al. | 47/1 R |
| 4,205,059 | 5/1980 | Hagens | 427/4 |
| 4,243,693 | 1/1981 | Nordh | 427/4 |

Primary Examiner—Michael R. Lusignan

[57] ABSTRACT

This invention relates to a method and composition for treatment of plants, and particularly to such methods and compositions as relieve weather induced stress in plants. In one specific form, the invention contemplates a composition for protecting a plant from damage by weather induced stress comprising an aqueous solution containing a quantity of dark hued vegetable dye effective for shading the leaves of the plant from the effects of sunlight, a quantity of an anti-transpiration agent effective for limiting transpiration of water from the plant, a quantity of agricultural streptomycin effective for suppressing growth of fungus otherwise possibly damaging to the plant, and a quantity of complexed mineral micronutrients effective for promoting plant growth and function. The composition is applied to plants in practicing the method of this invention, preferably by foliar application such as spraying.

24 Claims, No Drawings

METHOD AND COMPOSITION FOR TREATMENT OF PLANTS

FIELD AND BACKGROUND OF INVENTION

This invention relates to a method and composition for treatment of plants, and particularly to such methods and compositions as relieve weather induced stress in plants.

Many plants, and particularly grasses such as are used in golf course and other large area plantings, suffer from weather induced stress. Weather induced stress arises from conditions such as too little or too much moisture, intense sunlight and temperature, and the like and frequently causes plants to become hosts to fungal and other diseases which shorten the life of the plant. Where such plants represent a significant and/or important landscaping investment, such as is the case with a golf course, weather induced stress and the consequences of such stress become economically significant in addition to being significant as an appearance or visual factor. Most specifically, the loss of substantial grass areas in a golf course may result in both economic loss from loss of play and the need for additional economic investment in restoration of the affected areas.

BRIEF DESCRIPTION OF INVENTION

With the foregoing in mind, it is an object of this invention to facilitate protection of plants, and particularly of grasses, from weather induced stress and from the consequences otherwise possibly flowing from occurrences of such stress. In realizing this object of the present invention, a solution containing a dye, an anti-transpiration agent, a fungicide and nutrients is applied to the plant otherwise subjected to stress. The elements contained in the solution cooperate to shade the plant from the effects of excessive sunlight, control transpiration of moisture, suppress fungal growth otherwise occurring on transitions of humidity, and foster maintenance of plant growth during the time of weather stress.

Yet a further object of this invention is to provide a composition useful in maintaining stands of plants such as grass through intervals of weather induced stress of the type described. In realizig this object of the present invention, an aqueous solution is provided which contains non-toxic, organic and biodegradable agents including a dark hued dye such as blue or green vegetable dye; an anti-transpiration agent such as a wax; an agricultural fungicide such as streptomycin; and complexed mineral micronutrients, which components cooperate in the manner referred to above.

Yet a further object of this invention is to sustain plant material under adverse growing conditions related to drought and/or humidity changes which would otherwise induce growth of fungus which would destroy the plant material. In realizing this object of the invention, greenskeepers of golf courses who elect to respond to drought conditions by watering golf greens and the like may maintain playing conditions for a course while avoiding destruction of the grasses necessary to the greens as may otherwise occur.

DETAILED DESCRIPTION OF INVENTION

It is to be understood at the outset of the description which follows that persons of skill in the appropriate arts may modify the invention here described while still achieving the favorable results of this invention. Accordingly, the description which follows is to be understood as being a broad, teaching disclosure directed to persons of skill in the appropriate arts, and not as limiting upon the present invention.

In accordance with the present invention, plants are treated with an aqueous solution which contains a number of components which cooperate to protect the plants from weather induced stresses. In particular, grasses as used in golf courses and the like are subject to stress which can arise out of weather related conditions such as drought or lack of rain. Drought conditions are often met by a greenskeeper or other persons charged with maintenance of grassy areas by watering of the grassy areas. Watering under such conditions presents a number of problems, including the economic problems of supplying and delivering the water used and the plant growth problems of inducing fungus growth due to fluctuations in humidity levels to which the plants are exposed. The same or similar problems are encountered with other types of plant materials, and grasses are used here only as a teaching example and because grassy area maintenance provides a particularly graphic illustration of the benefits to be derived from the present invention.

In environments of the type described, the present invention accomplishes a method of protecting plants from damage by steps including preparing a solution containing a quantity of vegetable dye effective for shading the leaves of the plant from the effects of sunlight, a quantity of an anti-transpiration agent effective for limiting transpiration of water from the plant, a quantity of an agricultural fungicide effective for suppressing growth of fungus otherwise possibly damaging to the plant, and a quantity of complexed mineral micronutrients effective for promoting plant growth and function; and applying the solution to the plants. In the instance of grasses, the method as described has demonstrated the capability of maintaining a stand of grass in prime conditions through conditions which resulted in serious damage to other nearby stands of grass.

In practicing the method of the present invention, the following example may be followed:

EXAMPLE

Into five gallons of water, mix and dissolve:
- 16 ounces (fluid volume) of dry powder blue vegetable dye;
- 16 ounces (fluid volume) of aqueous paste wax anti-transpiration agent;
- 4 ounces (fluid volume) of dry powder agricultural streptomycin; and
- 16 ounces (fluid volume) of aqueous solution complexed mineral micronutrients.

Apply the resulting solution to grass by spraying.

When this example was followed for an application to seasonal rye grass in a Piedmont Carolinas location at which such grass normally dies due to heat and dryness by late spring, the stand was maintained for more than two months beyond the usual date of "browning off" with minimal watering and no occurrence of fungal disease. During the same interval of time, and a short interval thereafter, several golf courses in the general area of the test planting encountered loss of greens to fungus disease which was believed to have been induced and/or fostered by watering practices. Water application to maintain the test stand of grass in prime condition was significantly lower than originally anticipated.

It is believed that the function of the dye in the composition is that of shading the plant from the effects of excessive sunlight; the function of the anti-transpirant is that of controlling transpiratio of moisture and thereby reducing need for watering in order to maintain plant condition; the function of the streptomycin is to suppress growth of fungus otherwise induced or fostered by the variations in humidity following watering on a frequent or scheduled basis; and that the function of the complexed mineral micronutrients is to promote healthy plant growth during the interval of treatment with the solution of the present invention.

In developing the solution described above, it has been contemplated that at least certain of the components may be presently available materials. For example, the anti-transpiration agent may be such as are described in U.S. Pat. Nos. 3,791,839; 3,826,671; and 3,847,641 or such as is commercially available from Wilt-Pruf Products of Greenwich, Conn. The complexed micronutrients may be such as is commercially available from a number of sources, including Feast brand from Conklin Company, whose general crop mix contains iron, manganese and zinc complexed with ligninsulfonate. In the composition and method of the present invention, it is the cooperation of the components which is sought and which achieves the desired result.

It is also contemplated that certain components may be varied. More specifically, and by way of example only, a composition was prepared in accordance with another example in which the prior example was followed with the exception that the dark hued dye used was green. The composition was used in a foliar application by spraying, and the result obtained was essentially the same as reported above.

That which is claimed is:

1. A method of protecting a plant from damage by weather induced stress comprising preparing a solution containing a quantity of vegetable dye effective for shading the leaves of the plant from the effects of sunlight, a quantity of anti-transpiration agent effective for limiting transpiration of water from the plant, a quantity of an agricultural fungicide effective for suppressing growth of fungus otherwise possibly damaging to the plant, and a quantity of complexed mineral micronutrients effective for promoting plant growth and function, and applying the solution to the plant.

2. A method according to claim 1 wherein the step of applying the solution comprises spraying the solution onto the leaves of the plant.

3. The method according to one of claim 1 or claim 2 wherein the step of preparing the solution comprises mixing the dye, anti-transpiration agent, fungicide and complexed mineral micronutrients with water.

4. A method according to claim 3 wherein the step of preparing the solution comprises mixing a dark hued dye with the anti-transpiration agent, fungicide and complexed mineral micronutrients.

5. A method according to claim 4 wherein the dark hued dye is blue.

6. A method according to claim 4 wherein the dark hued dye is green.

7. A method according to claim 3 wherein the step of preparing the solution comprises mixing agricultural streptomycin with the dye, anti-transpiration agent, fungicide and complexed mineral micronutrients.

8. A method of protecting a plant from damage by weather induced stress comprising preparing an aqueous solution containing a quantity of dark hued vegetable dye effective for shading the leaves of the plant from the effects of sunlight, a quantity of an anti-transpiration agent effective for limiting transpiration of water from the plant, a quantity of agricultural streptomycin effective for suppressing growth of fungus otherwise possibly damaging to the plant, and a quantity of complexed mineral micronutrients effective for promoting plant growth and function, and spraying the solution onto the leaves of the plant.

9. A method according to claim 8 wherein the step of preparing the solution comprises mixing dry powder dye with water and the other constituents in a proportion of about 12.5% by volume of dye to the volume of water in the solution.

10. A method according to claim 8 wherein the step of preparing the solution comprises mixing an aqueous paste of the anti-transpiration agent with water and the other constituents in a proportion of about 12.5% by volume of anti-transpirant agent to the volume of water in the solution.

11. A method according to claim 8 wherein the step of preparing the solution comprises mixing dry powder streptomycin with water and the other constituents in a proportion of about 3% by volume of streptomycin to the volume of water in the solution.

12. A method according to claim 8 wherein the step of preparing the solution comprises mixing an aqueous solution of complexed mineral micronutrients with water and the other constituents in a proportion of about 12.5% by volume of nutrient solution to the volume of water in the solution.

13. A method of protecting a plant from damage by weather induced stress comprising preparing an aqueous solution containing, by volume with reference to the quantity of water, 12.5% of dry powder dark hued vegetable dye for shading the leaves of the plant from the effects of sunlight, 12.5% of an aqueous paste anti-transpiration agent for limiting transpiration of water from the plant, 3% of dry powder agricultural streptomycin for suppressing growth of fungus otherwise possibly damaging to the plant, and 12.5% of an aqueous solution of complexed mineral micronutrients for promoting plant growth and function, and spraying the solution onto the leaves of the plant.

14. A composition for protecting a plant from damage by weather induced stress comprising a solution containing a quantity of vegetable dye effective for shading the leaves of the plant from the effects of sunlight, a quantity of an anti-transpiration agent effective for limiting transpiration of water from the plant, a quantity of an agricultural fungicide effective for suppressing growth of fungus otherwise possibly damaging to the plant, and a quantity of complexed mineral micronutrients effective for promoting plant growth and function.

15. A composition according to claim 14 wherein the solution is aqueous.

16. A composition according to claim 15 wherein the dye is blue.

17. A composition according to claim 15 wherein the dye is green.

18. A composition according to claim 15 wherein the agricultural fungicide is streptomycin.

19. A composition for protecting a plant from damage by weather induced stress comprising an aqueous solution containing a quantity of dark hued vegetable dye effective for shading the leaves of the plant from the effects of sunlight, a quantity of an anti-transpiration agent effective for limiting transpiration of water from the plant, a quantity of agricultural streptomycin effective for suppresssing growth of fungus otherwise possibly damaging to the plant, and a quantity of complexed mineral micronutrients effective for promoting plant growth and function.

20. A composition according to claim 19 wherein the dye is mixed with the other constituents in a proportion of about 12.5% by volume of dry powder dye to the volume of water in the solution.

21. A composition according to claim 19 wherein the anti-transpiration agent is mixed with the other constituents in a proportion of about 12.5% by volume of aqueous paste anti-transpirant agent to the volume of water in the solution.

22. A composition according to claim 19 wherein the streptomycin is mixed with the other constituents in a proportion of about 3% by volume of dry powder streptomycin to the volume of water in the solution.

23. A composition according to claim 19 wherein the complexed mineral micronutrients are mixed with the other constituents in a proportion of about 12.5% by volume of an aqueous solution of nutrients to the volume of water in the solution.

24. A composition for protecting a plant from damage by weather induced stress comprising an aqueous solution containing, by volume with reference to the quantity of water, 12.5% of dry powder dark hued vegetable dye for shading the leaves of the plant from the effects of sunlight, 12.5% of an aqueous paste anti-transpiration agent for limiting transpiration of water from the plant, 3% of dry powder agricultural streptomycin for suppressing growth of fungus otherwise possibly damaging to the plant, and 12.5% of an aqueous solution of complexed mineral micronutrients for promoting plant growth and function.

* * * * *